United States Patent
Goto et al.

(10) Patent No.: US 9,125,809 B2
(45) Date of Patent: Sep. 8, 2015

(54) PECTIN-CONTAINING JELLY FORMULATION

(75) Inventors: Yoichiro Goto, Saitama (JP); Kurato Takanashi, Saitama (JP); Teruo Maruta, Saitama (JP); Masatake Dairaku, Saitama (JP)

(73) Assignee: NICHI-IKO PHARMACEUTICAL CO., LTD., Toyama (JP)

( * ) Notice: Subject to any disclaimer, the term of this patent is extended or adjusted under 35 U.S.C. 154(b) by 376 days.

(21) Appl. No.: 13/262,800

(22) PCT Filed: Apr. 3, 2009

(86) PCT No.: PCT/JP2009/056985
§ 371 (c)(1),
(2), (4) Date: Oct. 3, 2011

(87) PCT Pub. No.: WO2010/113324
PCT Pub. Date: Oct. 7, 2010

(65) Prior Publication Data
US 2012/0029017 A1 Feb. 2, 2012

(51) Int. Cl.
*A61K 9/56* (2006.01)
*A61K 9/00* (2006.01)
*A61J 1/06* (2006.01)

(52) U.S. Cl.
CPC ............... *A61K 9/0056* (2013.01); *A61J 1/067* (2013.01)

(58) Field of Classification Search
CPC ..................................... A61K 9/56; A61J 1/67
See application file for complete search history.

(56) References Cited

U.S. PATENT DOCUMENTS

| | | | |
|---|---|---|---|
| 6,403,140 B1 | 6/2002 | Tiainen et al. | |
| 2007/0014856 A1* | 1/2007 | Takagi et al. | 424/464 |
| 2007/0026075 A1* | 2/2007 | Shudo et al. | 424/488 |

FOREIGN PATENT DOCUMENTS

| | | |
|---|---|---|
| JP | 11-123231 | 5/1999 |
| JP | 2000-256181 | 9/2000 |
| JP | 2004-149469 | 5/2004 |
| JP | 2005-082536 | 3/2005 |
| JP | 2005-325081 | 11/2005 |
| JP | 2006-028028 | 2/2006 |
| JP | 2007-238561 | 9/2007 |
| JP | 2008-007420 | 1/2008 |
| JP | 2008-184400 | 8/2008 |
| JP | 2008-195714 | 8/2008 |
| JP | 2008-260708 | 10/2008 |
| JP | 2009-067790 | 4/2009 |
| WO | WO 2008/088039 | 7/2008 |

OTHER PUBLICATIONS

International Search Report dated Apr. 28, 2009 issued to international application No. PCT/JP2009/056985.
International Search Report dated Apr. 28, 2009 issued to international application No. PCT/JP2009/056986.
Journal of Pharmaceutical Science and Technology, Japan, vol. 67, supplement, p. 364, May 2007.
Machine Translation of Fumiko et al (JP 2007-238561 A published on Sep. 20, 2007).

\* cited by examiner

*Primary Examiner* — Wu-Cheng Winston Shen
*Assistant Examiner* — Christopher R Stone
(74) *Attorney, Agent, or Firm* — Knobbe, Martens, Olson & Bear, LLP

(57) ABSTRACT

There is disclosed a technique for making a jelly formulation comprising pectin slide out of a container easily (improving the slidability of the jelly formulation) when taking the formulation out of the container to prevent the formulation from remaining in the container. The jelly formulation of the present invention comprises a drug, pectin, divalent metal ions, and polyoxyethylene polyoxypropylene glycol.

4 Claims, 2 Drawing Sheets

[ ... ]

PECTIN-CONTAINING JELLY FORMULATION

CROSS-REFERENCE TO RELATED APPLICATIONS

This application is the U.S. National Phase under 35 U.S.C. §371 of International Application PCT/JP2009/056985 filed Apr. 3, 2009, which was published in a non-English language.

TECHNICAL FIELD

The present invention relates to a jelly formulation comprising pectin as a gelling agent.

BACKGROUND ART

In recent years, oral pharmaceutical formulations formulated in a jelly-like form for the purpose of masking the taste of a drug having an unpleasant taste or making it easier to swallow the drug, i.e., jelly formulations, have received much attention. Known gelling agents used to prepare a jelly formulation include carrageenan, pectin, agar, alginic acid, sodium alginate, gelatin, and xanthan gum (Patent Documents 1, 2, and 3). Among them, pectin is useful for a jelly formulation comprising a drug which is stable under acidic conditions, because it forms a jelly which is stable under acidic conditions by the presence of divalent metal ions such as calcium ions (Patent Documents 4, 5, and 6).

However, conventional jelly formulations comprising pectin have sticky properties (jam-like properties) on their surface. Jelly formulations are provided to patients generally encapsulated in a plastic container, and the jelly formulations having such sticky properties have had a problem in that they do not slide out of the container easily (poor slidability) when being taken out from the container. Because of the poor slidability, there has been a problem in that the formulations are prone to remain in the container and thus the administration of a predetermined amount of drug cannot be performed satisfactorily.

[Patent Document 1] JP 2008-195714 A
[Patent Document 2] JP 2008-260708 A
[Patent Document 3] JP 2006-28028 A
[Patent Document 4] JP 2008-184400 A
[Patent Document 5] JP 2007-238561 A
[Patent Document 6] JP 2005-325081 A

SUMMARY OF THE INVENTION

An object of the present invention is to provide a technique for making a jelly formulation comprising pectin easily slide out of a container (improving the slidability of the jelly formulation) when taking the formulation out from the container to prevent the formulation from remaining in the container.

The present inventors have found that blending a jelly formulation comprising pectin with polyoxyethylene polyoxypropylene glycol reduces the sticky properties of the jelly formulation comprising pectin. The present inventors then have found that a jelly formulation comprising pectin, wherein the jelly formulation is blended with polyoxyethylene polyoxypropylene glycol, easily slides out of a container (has a good slidability) when being taken out from the plastic container.

Thus, the present invention is as follows.

(1) A jelly formulation comprising a drug, pectin, divalent metal ions, and polyoxyethylene polyoxypropylene glycol (hereinafter referred to as "the jelly formulation of the present invention").

(2) The jelly formulation according to (1), wherein the polyoxyethylene polyoxypropylene glycol has an average degree of polymerization of polyoxyethylene from 3 to 200 and an average degree of polymerization of polyoxypropylene from 17 to 70.

(3) The jelly formulation according to (1) or (2), wherein the content of polyoxyethylene polyoxypropylene glycol is 0.001 to 0.5% by mass.

(4) The jelly formulation according to any one of (1) to (3), wherein the drug is donepezil hydrochloride.

(5) The jelly formulation according to (4), further comprising sodium chloride.

(6) A packaged jelly formulation comprising a plastic container and the jelly formulation according to any one of (1) to (5) encapsulated therein (hereinafter referred to as "the packaged jelly formulation of the present invention").

EMBODIMENTS FOR CARRYING OUT THE INVENTION

Figure 1:
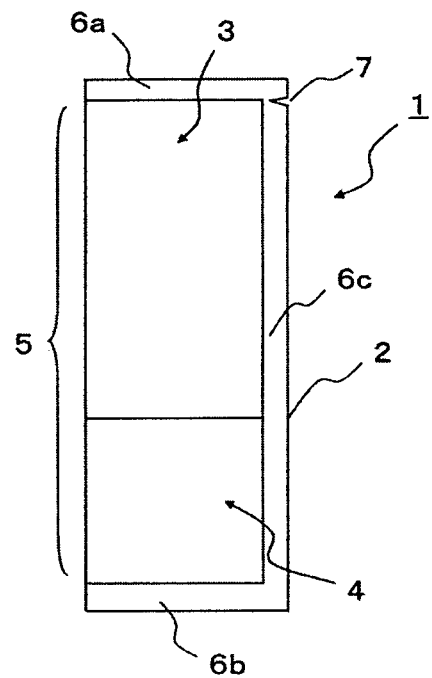
FIG. 1 shows a front view of the packaged jelly formulation 1 of the present invention.

The jelly formulation of the present invention comprises a drug, pectin, divalent metal ions, and polyoxyethylene polyoxypropylene glycol.

The drug is preferably, but not limited to, an acid-stable drug. Examples of the acid-stable drug include, e.g., hydrochlorides which are stable to pH about 2 to 5, such as donepezil hydrochloride, ketotifen fumarate, paeoniflorin hydrochloride, and ambroxol hydrochloride. The content of the drug in the jelly formulation of the present invention is determined depending, for example, on the type of the drug and the disease to which the drug is applied. For example, when the jelly formulation of the present invention comprises donepezil hydrochloride, the content thereof is generally 0.02 to 1% by mass, preferably 0.05 to 0.5% by mass.

Any pectin generally used in jelly formulations may be used without particular limitation. In the jelly formulation of the present invention, pectin having any degree of esterification may be used alone or in combination. As pectin used in the jelly formulation of the present invention, preferably, low methoxyl pectin (L.M. pectin) having a degree of esterification of about 40% or less (which is equivalent of methoxyl group content of about 7% or less) is used alone or in combination with high methoxyl pectin. As pectin used in the jelly formulation of the present invention, more preferably, pectin having a degree of esterification of 20 to 35% (which is equivalent of methoxyl group content of 3 to 5%) is used alone or in combination with pectin having a degree of esterification outside this range. In this case, the content of the pectin having a degree of esterification outside the above range is preferably not more than 50% by mass, more preferably not more than 30% by mass, and especially preferably not more than 10% by mass, based on the total content of pectin. As pectin used in the jelly formulation of the present invention, especially preferably, pectin having a degree of esterification of 20 to 35% is used alone.

The content of pectin in the jelly formulation of the present invention may be in the range in which a jelly soft enough to be easily swallowed (easily chewed in the oral cavity) can be formed. The content of pectin is generally 0.5 to 10% by mass, preferably 1 to 3% by mass.

Examples of divalent metal ions include, for example, calcium ions and magnesium ions. Divalent metal ions may be added to a formulation in the form of an orally acceptable metal salt. Examples of such calcium salts include, but not limited to, calcium disodium edetate, calcium chloride hydrate, calcium cellulose glycolate, calcium citrate, calcium gluconate hydrate, calcium acetate, calcium hydroxide, calcium stearate, calcium carbonate, calcium lactate hydrate, tricalcium phosphate, anhydrous dibasic calcium phosphate, and calcium sulfate. Examples of such magnesium salts include, but not limited to, magnesium L-aspartate, magnesium chloride, magnesium gluconate, magnesium silicate, aluminum magnesium silicate, magnesium aluminosilicate, magnesium oxide, aluminum magnesium hydroxide, magnesium hydroxide, aluminum hydroxide-magnesium carbonate-calcium carbonate coprecipitate, magnesium carbonate, magnesium stearate, and magnesium sulfate hydrate. In particular, preferred are calcium salts, among which calcium lactate is preferred. The content of divalent metal ions may be in the range in which a jelly soft enough to be easily swallowed can be formed. The content of divalent metal ions in the jelly formulation of the present invention is, in terms of metal amount, generally 0.0005 to 0.1% by mass, preferably 0.002 to 0.05% by mass. The content of divalent metal ions is, in terms of metal amount, generally 0.0003 to 0.1 parts by mass, preferably 0.001 to 0.05 parts by mass, based on 1 part by mass of pectin. When calcium ions are used, the content of calcium ions is, in terms of calcium amount, generally 0.001 to 0.1% by mass, preferably 0.005 to 0.05% by mass. The content of calcium ions is, in terms of calcium amount, generally 0.0007 to 0.07 parts by mass, preferably 0.0035 to 0.035 parts by mass, based on 1 part by mass of pectin.

Polyoxyethylene polyoxypropylene glycol used is, preferably, polyoxyethylene polyoxypropylene glycol having an average degree of polymerization in the polyoxyethylene moiety (the number of repetitions of a polyoxyethylene unit) from 3 to 200 and an average degree of polymerization of the polyoxypropylene moiety from 17 to 70, more preferably, polyoxyethylene polyoxypropylene glycol having an average degree of polymerization in the polyoxyethylene moiety from 120 to 200 and an average degree of polymerization of the polyoxypropylene moiety from 20 to 67, and especially preferably, polyoxyethylene polyoxypropylene glycol having an average degree of polymerization in the polyoxyethylene moiety from 120 to 160 and an average degree of polymerization of the polyoxypropylene moiety from 20 to 67.

Specific examples include polyoxyethylene (105) polyoxypropylene (5) glycol (each value in the parentheses indicates the average degree of polymerization), polyoxyethylene (120) polyoxypropylene (40) glycol (Pluronic F87), polyoxyethylene (160) polyoxypropylene (30) glycol (Pluronic F68), polyoxyethylene (42) polyoxypropylene (67) glycol (Pluronic P123), polyoxyethylene (54) polyoxypropylene (39) glycol (Pluronic P85), polyoxyethylene (196) polyoxypropylene (67) glycol (Pluronic F127), polyoxyethylene (20) polyoxypropylene (20) glycol (Pluronic L44), polyoxyethylene (200) polyoxypropylene (70) glycol, and polyoxyethylene (3) polyoxypropylene (17) glycol.

Polyoxyethylene (160) polyoxypropylene (30) glycol is most preferred. Polyoxyethylene (160) polyoxypropylene (30) glycol is commercially available under the trade name such as Pluronic F68 or Poloxamer 188.

The content of polyoxyethylene polyoxypropylene glycol may be in an amount acceptable for administration to a living body and in the range in which the jelly formation is not prevented. The content of polyoxyethylene polyoxypropylene glycol is preferably 0.001 to 0.5% by mass, more preferably 0.005 to 0.1% by mass. By using the content of polyoxyethylene polyoxypropylene glycol of not less than 0.001% by mass, the sticky properties of a jelly formulation are reduced, and the slidability of the jelly formulation improves (the jelly formulation encapsulated in a container easily slides out of the container when being taken out from the container.). By using the content of polyoxyethylene polyoxypropylene glycol of not less than 0.005% by mass, the sticky properties of a jelly formulation are reduced to almost nothing, and the slidability of the jelly formulation becomes excellent. Further, by using the content of polyoxyethylene polyoxypropylene glycol of not more than 0.5% by mass, preferably 0.1% by mass, foaming of a formulation can easily be prevented during the process for preparing the formulation, and a jelly formulation also excellent from the viewpoint of appearance, drug stability, and homogeneity of the formulation can be obtained.

The pH of the jelly formulation of the present invention may be in the range in which the jelly formation is not prevented. The pH of the jelly formulation of the present invention is preferably 2 to 5, more preferably 2.5 to 4.5. In this range, the stability of a jelly is especially good.

Examples of pH adjusters used to adjust the pH include organic acids such as citric acid, malic acid, tartaric acid, fumaric acid, phthalic acid, lactic acid, adipic acid, succinic acid, maleic acid, ascorbic acid, erythorbic acid, gluconic acid, and glycerophosphoric acid, and salts thereof; and inorganic acids such as hydrochloric acid and phosphoric acid, and salts thereof; amino acids such as glycine, alanine, and aspartic acid, and salts thereof; or alkaline agents such as sodium hydroxide and potassium hydroxide, and salts thereof Preferably, the jelly formulation of the present invention further comprises a component selected from sucrose, maltitol and C3-C4 alditols, and a component selected from C5-C6 alditols in combination. These components impart an appropriate rupture strength and high drug-release properties to the jelly formulation.

In the jelly formulation of the present invention, a component selected from sucrose, maltitol and C3-C4 alditols may be used alone or in combination. The total content of such components in the jelly formulation of the present invention is preferably 5 to 50% by mass, more preferably 10 to 50% by mass, and especially preferably 25 to 45% by mass.

Preferred examples of C3-C4 alditols include glycerin and erythritol. As these components, those commercially available may be used. A component selected from sucrose, maltitol and C3-C4 alditols have an effect of appropriately enhancing the rupture strength of a jelly formulation.

In the jelly formulation of the present invention, a component selected from C5-C6 alditols may be used alone or in combination.

The total content of such components in the jelly formulation of the present invention is preferably 5 to 30% by mass, more preferably 10 to 25% by mass. Preferred examples of C5-C6 alditols include xylitol and D-sorbitol. As these components, those commercially available may be used. A component selected from C5-C6 alditols have an effect of facilitating the above effect of a component selected from sucrose, maltitol and C3-C4 alditols to appropriately enhance the rupture strength of a jelly formulation, and an effect of enhancing the drug-release properties.

The mass ratio of the total content of a component selected from sucrose, maltitol and C3-C4 alditols to the total content of a component selected from C5-C6 alditols is preferably 1:0.1 to 1:3, more preferably 1:0.25 to 1:1.

The jelly formulation of the present invention may further contain additives generally used in medicaments as long as the jelly formation is not prevented and the above effects of polyoxyethylene polyoxypropylene glycol are not impaired. Examples of such optional components include antiseptics, sweetening agents, and flavoring agents.

The jelly formulation of the present invention, when comprising donepezil hydrochloride as a drug, preferably further comprises sodium chloride. Sodium chloride has an effect of reducing the bitterness of donepezil hydrochloride. The content of sodium chloride is preferably 0.01 to 1% by mass, more preferably 0.05 to 0.5% by mass. The content of sodium chloride is, based on 1 part by mass of donepezil hydrochloride, preferably 0.04 to 4 parts by mass, more preferably 0.2 to 2 parts by mass.

Thus, the present inventors found that sodium chloride reduces the bitterness of donepezil hydrochloride. Accordingly, the present invention also provides a medicament comprising donepezil hydrochloride and sodium chloride. Further, the present invention also provides a method of reducing the bitterness of donepezil hydrochloride, comprising adding sodium chloride to the medicament comprising donepezil hydrochloride. The preferred range of the content or additive amount of sodium chloride in this case is as described above. These inventions are applicable not only to the jelly formulation of the present invention but also to other jelly formulations or medicaments having dosage forms such as liquids, tablets, or granules.

Although the jelly formulation of the present invention may comprise gelling agents other than pectin, the content thereof is preferably less than 1 time by mass, more preferably less than 0.5 times by mass, and especially preferably less than 0.1 times by mass the content of pectin. More preferably, the jelly formulation of the present invention does not contain gelling agents other than pectin. If gelling agents other than pectin are contained in an amount equal to or more than the mass of pectin, the above effects of polyoxyethylene polyoxypropylene glycol can not be fully exerted.

The jelly formulation of the present invention can be prepared, for example, as described below.

Pectin, polyoxyethylene polyoxypropylene glycol, optionally, a component selected from sucrose maltitol, and C3-C4 alditols, and a component selected from C5-C6 alditols are added to purified water, and the resulting mixture is dissolved by heating at about 80° C. to 90° C. with stirring. A drug is added thereto, and the resulting mixture is dissolved (or mixed) with stirring. An aqueous solution of a divalent metal salt is added to the above dissolved (or mixed) solution to which the drug was added, and the resulting mixture is stirred. Thereafter, if needed, a pH adjuster is added to adjust the pH to around 2 to 5. The resulting dissolved (or mixed) solution is cooled to obtain the jelly formulation of the present invention.

The jelly formulation of the present invention is generally encapsulated in a plastic container, and stored and distributed as a packaged jelly formulation. The container is preferably made up of multilayer laminated films. The shape of the container is preferably a bar-like pouch. The container preferably comprises a pressure-deformable body portion for encupsuling therein the jelly formulation of the present invention and an opening means that forms an opening for discharging the jelly formulation outside the container by pressing the body portion.

The packaged jelly formulation of the present invention has, for example, such an enclosure form as described in, e.g., JP 3665498 B2, JP 2000-256181 A, JP 11-123231 A, and JP 09-194346 A.

Figure 2:
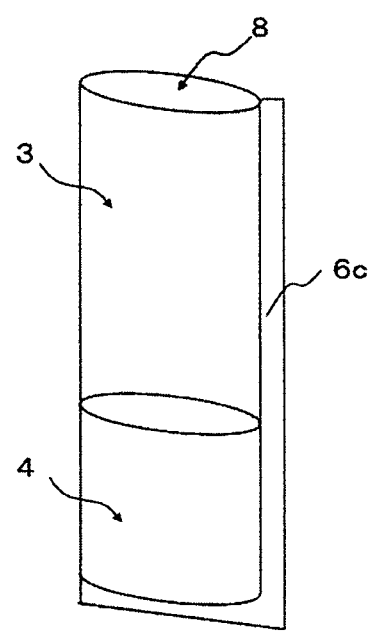
FIG. 2 shows a perspective view of the packaged jelly formulation 1 of the present invention in an opened state.

The packaged jelly formulation of the present invention preferably has the following form (for reference symbols, see FIG. 1 and FIG. 2).

A packaged jelly formulation comprising a bar-like pouch container (2) made of heat-sealable films and a jelly formulation of the present invention (3) encapsulated therein, wherein the container comprises a body portion (5) for encupsuling the jelly formulation and heat-sealed portions (6a, 6b, and 6c) formed on at least one end in the longitudinal direction of the body portion and on the side of the body portion, and a notch (7) (or a break line) for forming an opening (8) for discharging the jelly formulation outside the container is formed near either one end in the longitudinal direction of the body portion on the heat-sealed portion (6c).

Examples of the form of the packaged jelly formulation of the present invention include a packaged jelly formulation 1 shown in FIG. 1 (air-push type). FIG. 1 is a front view showing the packaged jelly formulation 1 of the present invention, and FIG. 2 a perspective view of the formulation in an opened state. In this form, the jelly formulation of the present invention (3) is encapsulated in the body portion together with a gas (4). The jelly formulation and the gas are encapsulated separately in two parts in the longitudinal direction of the body portion, and the pressure inside the body portion is equal to outside pressure, or it is higher than outside pressure, bringing the body portion into an inflated state. The notch or the break line is formed near the end of the side in which the jelly formulation is encapsulated in the longitudinal direction of the body portion on the heat-sealed portion (6c).

The packaged jelly formulation 1 of the present invention can be prepared by encupsuling the above-obtained dissolved (mixed) solution before being cooled, using a known method, in the container together with a gas. The enclosure method can be found in JP 2000-256181 A.

Alternatively, the jelly formulation of the present invention may be filled in the body portion (encapsulated without a gas).

EXAMPLES (1) Preparation of Packaged Jelly Formulation

According to the formulas shown in Table 1 and Table 2, packaged jelly formulations were prepared. The packaged jelly formulation of Example 1 was prepared as described below. Pectin, powdered hydrogenated maltose starch syrup (principal component: maltitol), xylitol, concentrated glycerin, and Pluronic F68 (polyoxyethylene (160) polyoxypropylene (30) glycol) were weighed and added to 30 mL of purified water, and the resulting mixture was dissolved by stirring with heating at 80 to 90° C. Donepezil hydrochloride was added thereto, and the resulting mixture was dissolved by stirring. Further, a calcium lactate aqueous solution (0.07 g of calcium lactate was dissolved in 5 mL of purified water) was added, and the resulting mixture was mixed by stirring with warming. To this mixture, a phosphoric acid aqueous solution (0.12 g of phosphoric acid was dissolved in 5 mL of purified water) was added to adjust the pH to around 3.5, a flavoring agent was added and mixed, and the rest of the purified water was added to a weight of 100 g. A single dose (2 g) each of the resulting dissolved solution was filled in a bar-like pouch container, encapsulated together with air, and cooled to obtain a packaged jelly formulation (air-push type, FIG. 1). The packaged jelly formulations of other Examples, Comparative Examples, and Reference Examples were prepared by the same method as for the packaged jelly formulation of Example 1. Sodium chloride, when added, was added together with pectin and the like to the mL of purified water described above.

(2) Evaluation of Slidability

Dischargeability of the packaged jelly formulations obtained was evaluated by three triers. By each trier, containers were opened from the notch formed on the containers, and the air-filled part of the body portion (see (4) in FIGS. 1 and 2) was pushed. The dischargeability of the jelly formulations was scored in accordance with the following criteria.
<Criteria>
5: Jelly formulation slid out well, and the jelly formulation was discharged extremely smoothly.
4: Jelly formulation slid out somewhat well, and the jelly formulation was discharged smoothly.
3: Jelly formulation slid out, and the jelly formulation was discharged without any problem.
2: Jelly formulation did not slide out easily, and the jelly formulation was hard to be discharged.
1: Jelly formulation did not slide out, and only air was discharged.
The results are shown in Table 1 and Table 2.

TABLE 1

| components (g) | Example 1 | Example 2 | Example 3 | Example 4 | Example 5 | Example 6 | Reference example 1 |
|---|---|---|---|---|---|---|---|
| donepezil hydrochloride | 0.25 | 0.25 | 0.25 | 0.25 | 0.25 | 0.25 | — |
| pectin | 1.4 | 1.4 | 1.4 | 1.4 | 1.4 | 1.4 | 1.4 |
| Pluronic F68 | 0.01 | 0.005 | 0.01 | 0.005 | 0.01 | 0.1 | 0.1 |
| erythritol | — | — | — | 25 | 25 | 25 | 25 |
| powdered hydrogenated maltose starch syrup | 25 | — | 30 | — | — | — | — |
| xylitol | 10 | 25 | — | 10 | 10 | 10 | 10 |
| concentrated glycerin | 15 | 30 | 10 | 15 | 15 | 15 | 15 |
| sodium chloride | — | — | — | 0.1 | 0.1 | 0.1 | 0.1 |
| calcium lactate | 0.07 | 0.07 | 0.07 | 0.07 | 0.07 | 0.07 | 0.07 |
| phosphoric acid | 0.12 | 0.11 | 0.11 | 0.12 | 0.12 | 0.12 | 0.12 |
| Japanese apricot flavoring agent | 0.1 | — | — | 0.05 | 0.05 | 0.05 | 0.05 |
| purified water | 48.05 | 43.165 | 58.16 | 48.005 | 48 | 47.91 | 48.16 |
| total | 100 | 100 | 100 | 100 | 100 | 100 | 100 |
| trier 1 | 5 | 4 | 5 | 4 | 5 | 5 | 4 |
| trier 2 | 5 | 4 | 5 | 4 | 5 | 5 | 4 |
| trier 3 | 5 | 4 | 5 | 4 | 5 | 5 | 4 |

TABLE 2

| components (g) | Comparative example 1 | Comparative example 2 | Comparative example 3 | Reference example 2 |
|---|---|---|---|---|
| donepezil hydrochloride | 0.25 | 0.25 | 0.25 | — |
| pectin | 1.4 | 1.4 | 1.4 | 1.4 |
| Pluronic F68 | — | — | — | — |
| erythritol | — | — | — | 25 |
| powdered hydrogenated maltose starch syrup | 25 | — | 30 | — |
| xylitol | 10 | 25 | — | 10 |
| concentrated glycerin | 15 | 30 | 10 | 15 |
| sodium chloride | — | — | — | 0.1 |
| calcium lactate | 0.07 | 0.07 | 0.07 | 0.07 |
| phosphoric acid | 0.12 | 0.11 | 0.11 | 0.12 |
| Japanese apricot flavoring agent | 0.1 | — | — | 0.05 |
| purified water | 48.06 | 43.17 | 58.17 | 48.26 |
| total | 100 | 100 | 100 | 100 |
| trier 1 | 1 | 1 | 1 | 1 |
| trier 2 | 1 | 1 | 1 | 1 |
| trier 3 | 1 | 1 | 1 | 1 |

From the comparison between Example 1 and Comparative Example 1, Example 2 and Comparative Example 2, and Example 3 and Comparative Example 3, it was proved that the addition of polyoxyethylene polyoxypropylene glycol markedly improves the slidability (dischargeability from a container) of jelly formulations. From the comparison between Reference Example 1 and Reference Example 2, neither of which comprises a drug, it was proved that the addition of polyoxyethylene polyoxypropylene glycol markedly improves the slidability (dischargeability from a container) of jelly bases themselves.

Even when the content of polyoxyethylene polyoxypropylene glycol was changed within the range of 0.005 to 0.1% by mass (Examples 4 to 6), the slidability (dischargeability from a container) was good. As is not shown in the above Table 1, for the formula in which the content of polyoxyethylene polyoxypropylene glycol was changed, the slidability (dischargeability from a container) was evaluated. The result was that when the content of polyoxyethylene polyoxypropylene glycol was less than 0.001% by mass, the slidability (dischargeability from a container) was worse than that of the above Examples, which was evaluated in accordance with the above criteria as scores 2 to 3.

When the content of polyoxyethylene polyoxypropylene glycol was more than 0.5% by mass, the formulation did not foam/defoam well and entrained the foam, resulting in decreased homogeneity of the formulation.

(3) Measurement of Residual Amount of Jelly Formulation in Container

For the packaged jelly formulations of Example 3, Comparative Example 3, and Reference Examples 1 and 2 prepared above, the residual amount of the jelly formulations in the container was measured.

For each packaged jelly formulation (2 g of the jelly formulation was encapsulated), by three triers, the air-filled part of the body portion was pushed three times per trier in the same manner as in the above (2), after which the residual amount of the jelly formulations in the container was measured, and the residual rate of the jelly formulations was calculated (each n=9).

The results are shown in Table 3.

TABLE 3

|  | Example 3 | Comparative example 3 | Reference example 1 | Reference example 2 |
|---|---|---|---|---|
| average residual amount of jelly formulation in container (g) | 0.017 | 1.971 | 0.015 | 1.987 |
| residual rate of jelly formulation (% by mass) | 0.85 | 99 | 0.75 | 99 |

(each: n = 9)

In the packaged jelly formulations of Example 3 and Reference Example 1, both of which comprises polyoxyethylene polyoxypropylene glycol, the residual rate of the jelly formulation in the container was less than 1% by mass. On the other hand, in the packaged jelly formulations of Comparative Example 3 and Reference Example 2, neither of which comprises polyoxyethylene polyoxypropylene glycol, the residual rate of the jelly formulation in the container was about 99% by mass.

From these results, it was proved that the addition of polyoxyethylene polyoxypropylene glycol is important especially when an air-push type container as shown in FIG. 1 is used.

(4) Evaluation of Taste

The taste of the jelly formulation of Example 5 prepared above and the jelly formulation of Example 7 shown in Table 4 was evaluated by three triers in accordance with the following criteria, and the average score was calculated.
<Criteria>
5: Taste sweet, and no problem in taking.
4: Taste sweet, no problem in taking, but slightly feel other taste.
3: Taste sweet, but slightly feel bitter taste separately.
2: Feel sweet taste and bitter taste separately, but can be taken with endurance.
1: Feel sweet taste and bitter taste separately, and hard to be taken.

The results are shown in Table 4.

TABLE 4

| components (g) | Example 5 | Example 7 |
|---|---|---|
| donepezil hydrochloride | 0.25 | 0.25 |
| pectin | 1.4 | 1.4 |
| Pluronic F68 | 0.01 | 0.01 |
| erythritol | 25 | 25 |
| powdered hydrogenated maltose starch syrup | — | — |
| xylitol | 10 | 10 |
| concentrated glycerin | 15 | 15 |
| sodium chloride | 0.1 | — |
| calcium lactate | 0.07 | 0.07 |
| phosphoric acid | 0.12 | 0.12 |
| Japanese apricot flavoring agent | 0.05 | 0.05 |
| purified water | 48 | 48.1 |
| total | 100 | 100 |

TABLE 4-continued

| components (g) | Example 5 | Example 7 |
|---|---|---|
| trier 1 | 5 | 2 |
| trier 2 | 5 | 2 |
| trier 3 | 4 | 2 |

From these results, it was proved that the blending with sodium chloride mildens the bitterness of donepezil hydrochloride.

(5) Preparation of Packaged Jelly Formulation

According to the formulas shown in Table 5, packaged jelly formulations were prepared. The packaged jelly formulation of Example A was prepared as described below. Pectin, powdered hydrogenated maltose starch syrup (principal component: maltitol), xylitol, concentrated glycerin, and Pluronic F68 (polyoxyethylene (160) polyoxypropylene (30) glycol) were weighed and added to 30 mL of purified water, and the resulting mixture was dissolved by stirring with heating at 80 to 90° C. Donepezil hydrochloride was added thereto, and the resulting mixture was dissolved by stirring. Further, a calcium lactate aqueous solution (0.07 g of calcium lactate was dissolved in 5 mL of purified water) was added, and the resulting mixture was mixed by stirring with warming. To this mixture, a phosphoric acid aqueous solution (0.12 g of phosphoric acid was dissolved in 5 mL of purified water) was added to adjust the pH to around 3.5, and the rest of the purified water was added to a weight of 100 g. A single dose (2 g) each of the resulting dissolved solution was filled in a bar-like pouch container, encapsulated together with air, and cooled to obtain a packaged jelly formulation (air-push type, FIG. 1). The jelly formulations of Examples B and C were prepared by the same method as in Example A.

TABLE 5

| components (g) | Example A | Example B | Example C |
|---|---|---|---|
| donepezil hydrochloride | 0.25 | 0.25 | 0.25 |
| pectin | 1.4 | 1.4 | 1.4 |
| Pluronic F68 | 0.01 | 0.01 | 0.01 |
| powdered hydrogenated maltose starch syrup | 30 | 30 | 30 |
| concentrated glycerin | 10 | 10 | 10 |
| xylitol | 10 | 20 | 0 |
| calcium lactate | 0.07 | 0.07 | 0.07 |
| phosphoric acid | 0.12 | 0.12 | 0.12 |
| purified water | 48.15 | 38.15 | 58.15 |
| total | 100 | 100 | 100 |
| trier 1 | 5 | 4 | 5 |
| trier 2 | 5 | 4 | 5 |
| trier 3 | 5 | 4 | 5 |

(6) Measurement of Rupture Strength

The packaged jelly formulations of the above Examples were left to stand at room temperature (25° C.) for 24 hours, after which the jelly formulations were taken out of the container, and the rupture strength of the jelly formulations was measured.

The rupture strength (g) was measured at Mode 4, a measuring speed of 30 mm/min, an adapter 8 mm in diameter (cylindrical), and room temperature (25° C.), using a rheometer (CR500DX manufactured by Sun Scientific Co. Ltd.).

Figure 3:
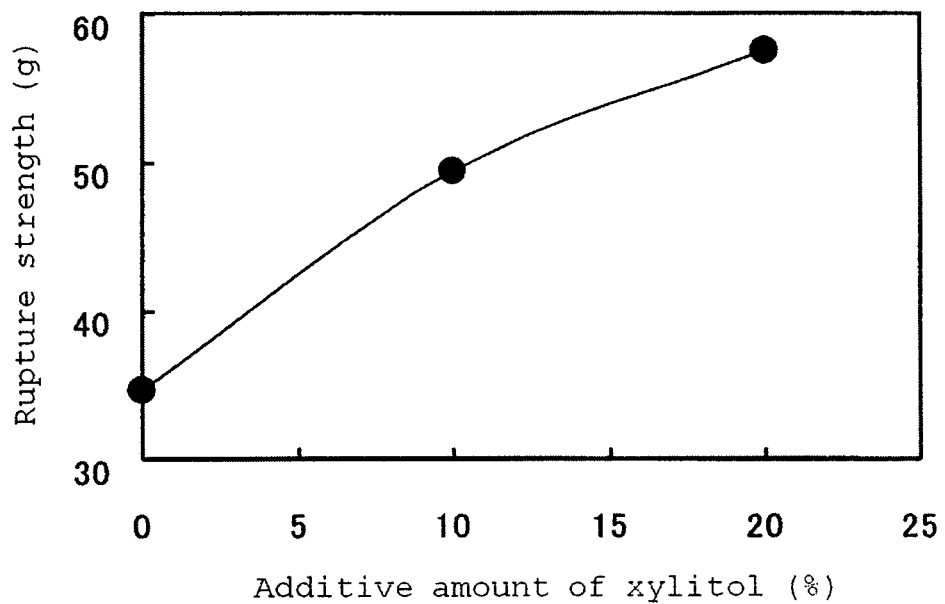
FIG. 3 shows the relationship between the additive amount of xylitol and the rupture strength of a jelly formulation.

The results are shown in FIG. 3.

As can be seen from FIG. 3, the larger the additive amount of xylitol, the stronger the rupture strength of the jelly formulation. When based on the rupture strength obtained by this measurement method, a jelly formulation in the range of 40 to 120 g can be said to be a jelly formulation having ideal physical properties, which has such a strength that it does not crumble during normal distribution and storage as well as under pressure that can be applied by, e.g., extrusion from the pouch container as described above, but crumbles upon chewing. From these, the content of xylitol in the jelly formulation of the present invention is especially preferably about 5 to 30% by mass. The content of xylitol is especially preferably about 0.12 to 0.75 times by mass based on 1 part by mass of sucrose and C3-C4 alditols.

(7) Measurement of Drug-Release Rate

The drug release rate of the jelly formulations of the above Examples was measured by the following method. The measurement was performed in accordance with the "paddle method" of "dissolution test method" in JP XV (Japanese Pharmacopoeia 15th edition). Purified water (900 mL) was used as an eluate, to which each jelly formulation was added, and the drug concentration (%) over time in the eluate was measured by spectrophotometry.

Figure 4:
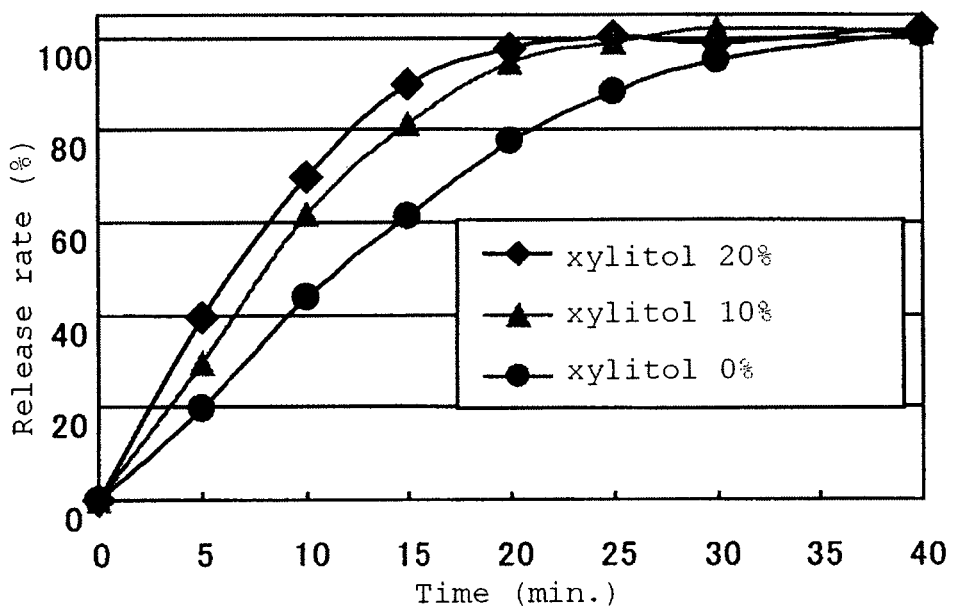
FIG. 4 shows the relationship between the standing time of jelly formulations and the release rate of drug from the jelly formulations.

The results are shown in FIG. 4.

As can be seen from FIG. 4, the larger the content of xylitol, the shorter the time until the drug release rate of the jelly formulation exceeds a certain value. For example, in the jelly formulation comprising no xylitol, it took about 30 minutes until exceeding the release rate of 90%; in the jelly formulation comprising 10% by mass of xylitol, it took about 20 minutes until exceeding the release rate of 90%; and in the jelly formulation comprising 20% by mass of xylitol, it took about 15 minutes until exceeding the release rate of 90%. Further, in the jelly formulation comprising no xylitol, it took about 40 minutes until reaching the release rate of 100%; in the jelly formulation comprising 10% by mass of xylitol, it took about 30 minutes until reaching the release rate of 100%; and in the jelly formulation comprising 20% by mass of xylitol, it took about 20 minutes until reaching the release rate of 100%.

Taken together with the test results of the above (6), it is particularly noteworthy that the blending a jelly formulation comprising pectin with xylitol increased the rupture strength of the jelly formulation (hardened the jelly formulation) and at the same time improved the drug-release properties.

INDUSTRIAL APPLICABILITY

The jelly formulation of the present invention, when being taken out of a plastic container, easily slides out of the container (has a good slidability). The jelly formulation of the present invention can provide, especially when a single-use pouch container is used, satisfactory taking of a predetermined amount of drug without leaving the formulation in the container. The jelly formulation of the present invention is suitable for a medicament comprising an acid-stable drug. The jelly formulation of the present invention is particularly suitable for a formulation comprising donepezil hydrochloride known as a dementia drug.

DESCRIPTION OF SYMBOLS

1 Packaged jelly formulation
2 Pouch container
3 Jelly formulation
4 Gas
5 Body portion
6a, 6b, and 6c Heat-sealed portions
7 Notch
8 Opening

What is claimed is:

1. A jelly formulation comprising a drug, pectin, divalent metal ions, and polyoxyethylene (160) polyoxypropylene (30) glycol, wherein the content of polyoxyethylene (160) polyoxypropylene (30) glycol is 0.001 to 0.5% by mass.

2. The jelly formulation according to claim 1, wherein the drug is donepezil hydrochloride.

3. The jelly formulation according to claim 2, further comprising sodium chloride.

4. A packaged jelly formulation comprising a plastic container, wherein said plastic container comprises the jelly formulation according to claim 1.

* * * * *

UNITED STATES PATENT AND TRADEMARK OFFICE
CERTIFICATE OF CORRECTION

PATENT NO.       : 9,125,809 B2
APPLICATION NO.  : 13/262800
DATED            : September 8, 2015
INVENTOR(S)      : Yoichiro Goto et al.

Page 1 of 1

It is certified that error appears in the above-identified patent and that said Letters Patent is hereby corrected as shown below:

In the Specification

In column 4 at line 37, Change "thereof" to --thereof.--.

In column 7 at line 5, Change "the mL" to --30 mL--.

Signed and Sealed this
Third Day of May, 2016

Michelle K. Lee
*Director of the United States Patent and Trademark Office*